United States Patent [19]
Bohner et al.

[11] 3,973,011
[45] Aug. 3, 1976

[54] OXADIAZOLYLPHOSPHORUS COMPOUNDS FOR COMBATTING INSECTS AND ACARIDES

[75] Inventors: Beat Bohner, Binningen; Willy Meyer, Basel, both of Switzerland

[73] Assignee: Ciba-Geigy Corporation, Ardsley, N.Y.

[22] Filed: June 11, 1975

[21] Appl. No.: 585,992

Related U.S. Application Data

[60] Division of Ser. No. 417,697, Nov. 20, 1973, Pat. No. 3,903,100, which is a continuation-in-part of Ser. No. 230,041, Feb. 28, 1972.

[30] Foreign Application Priority Data

Mar. 17, 1971  Switzerland.......................... 3930/71
Jan. 25, 1972  Switzerland.......................... 1075/72

[52] U.S. Cl............................. 424/200; 424/DIG. 8
[51] Int. Cl.²............................................ A01N 9/36
[58] Field of Search...................... 424/200, DIG. 8

[56] References Cited
UNITED STATES PATENTS 3,666,768  5/1972  Barker........................... 424/200 X

FOREIGN PATENTS OR APPLICATIONS 652,050  12/1964  Belgium
1,213,707  11/1970  United Kingdom

*Primary Examiner*—Albert T. Meyers
*Assistant Examiner*—Allen J. Robinson
*Attorney, Agent, or Firm*—Harry Falber

[57] ABSTRACT

Insecticidal and acaricidal composition and method utilizng oxadiazolyl compounds of the formula

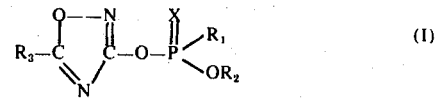

(I)

wherein $R_1$ represents alkyl, alkoxy or phenyl, $R_2$ represents alkyl, $R_3$ represents hydrogen, alkyl, alkenyl, alkinyl, phenyl, benzyl, phenoxy, alkoxy, carbamoyl, mono- and dialkyl carbamoyl, or alkoxy carbonyl, and X represents oxygen or sulphur.

10 Claims, No Drawings

OXADIAZOLYLPHOSPHORUS COMPOUNDS FOR COMBATTING INSECTS AND ACARIDES

This is a divisional of application Ser. No. 417,697 filed on Nov. 20, 1973, now U.S. Pat. No. 3,903,100 which in turn is a continuation-in-part of application Serial No. 230,041, filed February 28, 1972 now abandoned.

The present invention relates to oxadiazolyl compounds, their manufacture and their use in pest control.

The oxadiazolyl compounds correspond to the formula

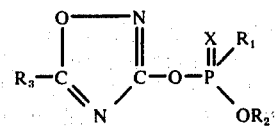

(I)

wherein $R_1$ represents alkyl, alkoxy or phenyl, $R_2$ represents alkyl, $R_3$ represents hydrogen, alkyl, alkenyl, alkinyl, phenyl, benzyl, phenoxy, alkoxy, carbamoyl, mono- and dialkyl carbamoyl or alkoxy carbonyl, and X represents oxygen or sulphur.

The alkyl, alkenyl, alkinyl and alkoxy chains represented by $R_1$, $R_2$ and $R_3$ contain from 1 to 18 or 2 to 18 carbon atoms (in the case of the alkenyl and alkinyl radicals), but preferably from 1 to 4 or 2 to 4 carbon atoms, and may be branched or straight-chain. Examples of such radicals include: methyl, methoxy, ethyl, ethoxy, propyl, propoxy, isopropyl, n-, i-, sec. and tert. butyl, allyl, crotonyl, methallyl, propargyl, n-butinyl.

Importance attaches to compounds of the formula

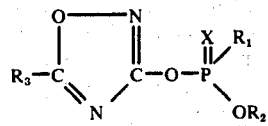

(II)

wherein $R_1$ represents $C_1-C_4$ alkyl, $C_1-C_4$ alkoxy or phenyl, $R_2$ represents $C_1-C_4$ alkyl, $R_3$ represents $C_1-C_4$ alkyl, $C_2-C_4$ alkenyl, $C_2-C_4$ alkinyl,

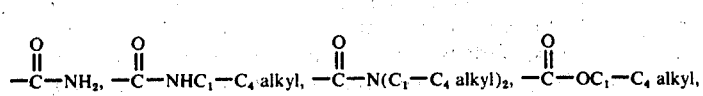

phenyl or benzyl and X represents oxygen or sulphur, and particularly to the compounds of the formula

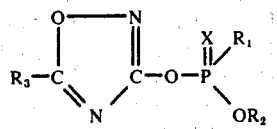

(III)

wherein $R_1$ represents $C_1-C_4$ alkyl or $C_1-C_4$ alkoxy; $R_2$ represents $C_1-C_4$ alkyl; and $R_3$ represents $C_1-C_4$ alkyl, benzyl or phenyl.

The compounds of formula (I) are manufactured according to the invention by a. reacting a hydroxyoxadiazole of the formula

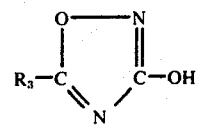

(IV)

with a phosphoric halide of the formula

(V)

in the presence of an acid binding agent, or b. reacting a salt of a hydroxyoxadiazole of the formula (IV) with a phosphoric halide of the formula (V).

In the formulae (IV), and (V), the symbols $R_1$, $R_2$, $R_3$ and X have the meanings given for the formula (I) and Hal represents fluorine, chlorine, bromine or iodine, but particularly chlorine or bromine.

As salts of hydroxydiazoles of the formula (IV) which are suitable for the process according to the invention there may be used, for example, salts of monovalent metals, in particular the alkali metal salts.

The following bases, for example, are suitable as acid binding agents: tertiary amines, such as triethylamine, dimethyl aniline, pyridine, pyridine bases; inorganic bases, for example hydroxides and carbonates of alkali and alkaline earth metals, preferably sodium and potassium carbonate.

It is advisable to carry out the reaction in inert solvents, for which purpose the following may be cited as suitable: aromatic hydrocarbons, such as benzene, toluene, petroleum ethers, chlorobenzene, polychlorobenzenes, bromobenzene; chlorinated alkanes containing from 1 to 3 carbon atoms; ethers, such as dioxan, tetrahydrofuran; esters, such as ethyl acetate; ketones, such as methyl ethyl ketone, diethyl ketone; nitriles, such as acetonitrile, Some of the starting materials of the formula (IV) are known compounds. It is possible to manufacture them by the process described in Comp.Rend. 26 (1), 174-177 (1965), G. Baccar and F. Mathis, or by the new synthesis routes:

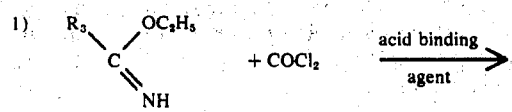

-continued

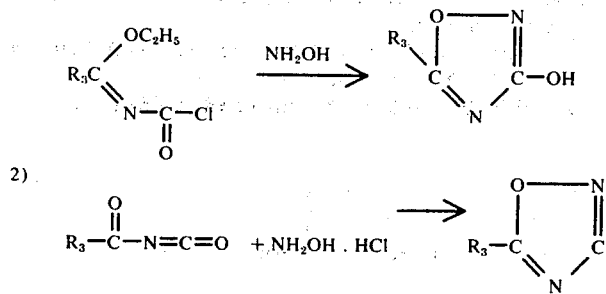

2)

$$R_3-\overset{O}{\overset{\|}{C}}-N=C=O + NH_2OH \cdot HCl \longrightarrow R_3-C\underset{N}{\overset{O----N}{\diagdown\diagup}}C-OH$$

In the formulae, $R_3$ has the same meaning as in formula I.

The active substances of the formula I are suitable for combating animal and plant pests of the most diverse kinds. Above all, however, they are active against all development stages, such as eggs, larvae, nymphs, pupae and adults of insects and representatives of the order acarina, such as mites and ticks.

The compounds of the formula I may be used, for example, against the following insects and representatives of the order acarina: insects of the families:

| | |
|---|---|
| Tetrigonidae | Tenebrionidae |
| Gryllidae | Chrysomelidae |
| Gryllotalpidae | Bruchidae |
| Blattidae | Tineidae |
| Peduviidae | Noctindae |
| Phyrrhocoriae | Lymatriidae |
| Cimicidae | Pyralidae |
| Delphacidae | Culicidae |
| Aphididae | Tipulidae |
| Diaspididae | Stomoxydae |
| Pseudococcidae | Trypetidae |
| Scarabaeidae | Muscidae |
| Dermestidae | Calliphoridae and |
| Coccinellidae | Pulicidae |

Acarida of the families:
 Ixodidae
 Argasidae
 Tetranychidae and
 Dermanyssidae.

The insecticidal and/or acaricidal action can be substantially broadened and adapted to suit the particular circumstances by the addition of other insecticides and/or acaricides.

Suitable additives include, for example, the following active substances: — organic derivatives of phosphorus, formamidines, ureas, carbamic acid derivatives, and chlorinated hydrocarbons. —

Moreover, the compounds of the formula I possess nematocidal properties and may be used, for example, to combat a wide variety of plant parasitic nematodes.

The compounds of the formula I may be used as pure active substance or together with suitable carriers and/or additives. Suitable carriers and additives can be solid or liquid and correspond to the substances conventionally used in formulation technique such as, for example, as solvents dispersants, wetting agents, adhesives, thickeners, binders and/or fertilisers.

For application, the compounds of the formula I may be processed to dusts, emulsion concetrates, granules, dispersions, sprays, to solutions, or suspensions in the conventional formulation which is commonly employed in application terminology. Mention may also be made of ("cattle dips" and "spray races", in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may be available and can be used in the following forms:
Solid forms:
  Dusts, tracking agents, granules, coated granules, impregnated granules and homogeneous granules.
Liquid forms:
  a. active substances which are dispersible in water: wettable powders, pastes, emulsions;
  b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminum silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used alone or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/ desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carries and subsequently comminuting the product.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (Carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilize the active substance, surface-active substance and anti-foam agents and, optionally, solvents.

Wettable powder and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and formaldehyde, as well as alkali, ammonium and alkaline earth metal salts or lignin sulfonic acid, in addition, alkylaryl sulfonates, alkali and alkaline earth metal salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleoyl ethionate, the sodium salt of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives mentioned above that, in wettable powder, the solid particle size of from 0.02 to 0.04 and in pastes, of 0.03 is not exceeded. To produce emulsifiable concentrates and pastes, dispersing agents such as those cited above, organic solvents and water are used. Examples of suitable solvents are the following: alcohols, benzene, xylene, toluene, dimethyl sulfoxide, and mineral oil fractions boiling between 120° and 350°C. The solvents must be practically odorless, not phytotoxic, inert to the active substances and not readily inflammable.

Furthermore, the agents according to the invention can be applied in the form of solutions. For this purpose the active substance or several active substances of the general formula I are dissolved in suitable organic solvents, mixtures of solvents or in water. Aliphatic and aromatic hydrocarbons, chlorinated derivatives thereof, alkyl naphthalenes, and mineral oils alone or mixed with each other, can be used as organic solvents.

The content of active substance in the above described agents is between 0.1% to 95% in which connection it should be mentioned that in the case of application from aircraft or some other suitable means of application, it is possible to use concentrations of up to 99.5% or even pure active substance.

The active substances of the formula I can, for example, be formulated as follows:

Dusts

The following substances are used to manufacture a) a 5% and b) a 2% dust:
a.
 5 parts of active substance
 95 parts of talcum
b.
 2 parts of active substance
 1 part of highly disperse silica
 97 parts of talcum.

The active substances are mixed with the carriers and ground.

Granules

The following substances are used to produce 5% granules:
 5 parts of active substance,
 0.25 parts of epichlorohydrin,
 0.25 parts of cetyl polyglycol ether,
 3.50 parts of polyethylene glycol,
 91 parts of kaolin (particle size 0.3 - 0.8 mm).

The active substance is mixed with epichlorohydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder:

The following constituents are used for the preparation of a) a 40%, b) and c) a 25%, and d) a 10% wettable powder:
a.
 40 parts of active substance,
 5 parts of sodium lignin sulphonate,
 1 part of sodium dibutyl-naphthalene sulphonate,
 54 parts of silica acid.
b.
 25 parts of active substance,
 4.5 parts of calcium lignin sulphonate
 1.9 parts of Champagne chalk/hydroxyethyl cellulose mixture (1:1),
 1.5 parts of sodium dibutyl naphthalene sulphonate,
 19.5 parts of silica acid,
 19.5 parts of Champagne chalk.
 28.1 parts of kaolin.
c.
 25 parts of active substance,
 2.5 parts of isooctylphenoxy-polyoxyethylene-ethanol,
 1.7 parts of Champagne chalk-hydroxyethyl cellulose mixture (1:1),
 8.3 parts of sodium aluminium silicate,
 16.5 parts of kieselguhr, 46 parts of kaolin.

d.
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powder are obtained which can be diluted with water to give suspensions of any desired concentration.

Emulsifiable concentrates:

The following substances are used to produce a) a 10% and b) a 25% emulsifiable concentrate:

a.
10 parts of active substance,
3.4 parts of epoxidised vegetable oil,
13.4 parts of a combination emulsifier consisting of fatty alcohol polyglycol ether and alkylarylsulphonate calcium salt,
40 parts of dimethylformamide,
43.2 parts of xylene.

b.
25 parts of active substance,
2.5 parts of epoxidised vegetable oil,
10 parts of an alkylarylsulphonate/fatty alcohol-polyglycol ether mixture
5 parts of dimethylformamide,
57.5 parts of xylene.

From these concentrates it is possible to produce, by dilution with water, emulsion of any desired concentration.

Spray:

The following constituents are used to prepare a 5% spray:
5 parts of active substance,
1 part of epichlorohydrin,
94 parts of benzene (boiling limits 160° – 190°C).

EXAMPLE 1

A. Manufacture of 0,0-diethyl-0-[5-phenyl-1,2,4-oxadiazolyl-(3)]-thiophosphate

Manufacture of the starting material a. Within 30 minutes 1 mol of benzimidoethyl ether added dropwise at 0°–10°C to 0.6 mols of phosgene in 500 ml of toluene. After stirring for 1 hour at 0°–10°C, nitrogen was blown through the suspension. Upon filtering off the precipitated benzimidoethyl ether hydrochloric, the filtrate was concentrated, leaving as residue the not very stable acid chloride of the formula

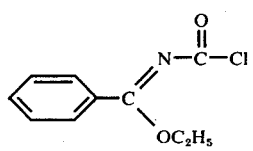

b. 29.9 Grams of hydroxylamine hydrochloric 64 ml of pyridine and 600 ml of toluene were boiled for 30 minutes. After the mixture had cooled to 20°C, 76.3 g of the compound of the formula

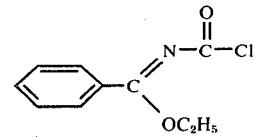

dissolved in 200 ml of tetrahydrofuran were added dropwise at 20°–30°C within 20 minutes.

The suspension was wholly concentrated after being boiled for 3 hours and the residue treated with 300 ml of water.

The precipitated crystals of the compound of the formula

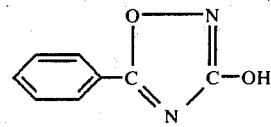

have a melting point of 198°–199°C after processing and recrystallisation from toluene.

Manufacture of Active Substance No. 1

16.2 Grams of 3-hydroxy-5-phenyl-1,2,4-oxadiazole, 13.85 g of $K_2CO_3$ and 280 ml of acetonitrile were stirred for 2 hours at 70°C. After the suspension had cooled to 50°C, 15.8 ml of chlorothiophosphoric diethyl ester in 85 ml of acetonitrile were added dropwise within 30 minutes. After being stirred for 22 hours at 50°–55°C, the suspension was cooled to 20°C, filtered and completely concentrated. After chromatography over silica gel the active substance of the formula

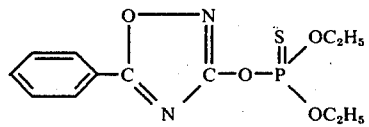

was obtained in the form of a pale yellow liquid with a refraction index of $n_D^{20}$ 1.5388.

B. Manufacture of 0,0-diethyl-0-[5-t-butyl-1,2,4-oxadiazolyl-(3)]-thiophosphate

Manufacture of the starting material

A suspension of 14.4 g of hydroxylamine hydrochloride and 28.5 g of potassium carbonate in 300 ml of tetrahydrofuran was heated for 2 hours to reflux. 25.4 Grams of $(CH_3)_3$-CO-NCO were then added dropwise at 30°–35°C within 20 minutes. The mixture was heated to reflux for 2 hours, the undissolved salts were filtered off and the solvent evaporated in vacuo. The residue was taken up in 2NaOH and extracted once with ethyl acetate. After the aqueous phase had been acidified with 2N HCl, the compound of the formula -continued

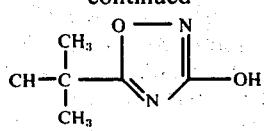

crystallised out.

After recrystallisation from ether, the melting point was 97°–99°C.

Manufacture of Active Substance No. 2

16.1 Grams of $K_2CO_3$ were added to a solution of 16.6 g of 3-hydroxy-5-t-butyl-1,2,4-oxadiazole in 290 ml of methyl ethyl ketone. After 2 hours stirring at 70°C, the mixture was cooled to 50°C, 21.7 g of chlorothiophosphoric diethyl ester in 90 ml of methyl ketone were added and the batch was stirred for 20 hours at 50°–55°C. The undissolved salts were filtered off and the filrate was freed from solvent in vacuo, when 33.4 g of active substance of the formula

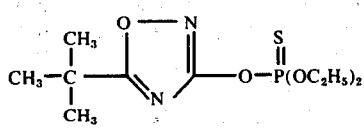

were obtained in the form of a pale yellow oil with a refractive index of $n_D^{20}$ 1.6687.

The following compounds were manufactured in analogous manner:

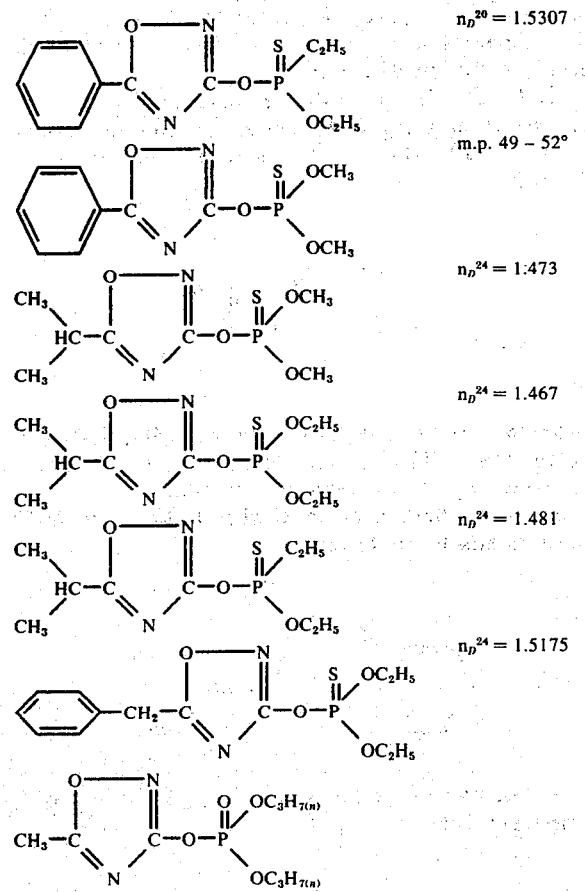

-continued

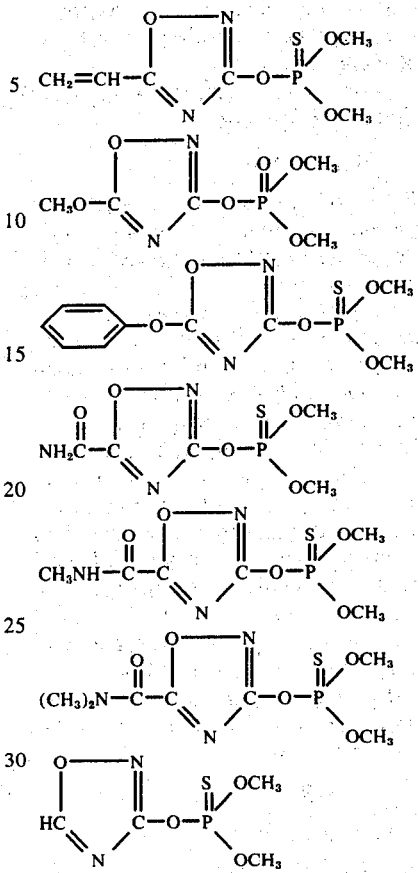

EXAMPLE 2

A. Insecticidal ingest poison action

Tobacco and potato plants are sprayed with a 0.05% aqueous emulsion (obtained from a 10% emulsifiable concentrate).

After the coating has dried, Egyptian cotton leaf worms (*Spodoptera literalis*) are settled on the tobacco plants and Colarado potato bettle larvae (*Leptinotarsa decemlineata*) on the potato plants. The test is carried out at 24°C and 60% relative humidity.

B. Systemic insecticidal action

To determine the systemic action, rooted bean plants (*Vicia fabae*) are put into a 0.01% aqueous active substance solution (obtained from a 10% emulsifiable concentrate). After 24 hours, aphids (*Aphis fabae*) are placed on the parts of the plant above the soil. The aphids are protected from contact and gas action by means of a special device. The test is carried out at 24°C and 70% relative humidity. In the above tests the compounds according to Example I displayed good insecticidal ingest poison action and septemic insecticidal action.

EXAMPLE 3

Action against *Chilo suppressalis*

Six rice plants at a time of the variety Caloro were transplanted into plastic pots (diameter at the top = 17 cm) and reared to a height of about 60 cm. Infestation with *Chilo suppressalis* larvae ($L_1$: 3-4 mm long) took place against 2 days after application of the active substance in granule form to the paddy water (rate of application: 8 kg of active substance per hectare). Evaluation of the insecticidal action took place 10 days after application of the granules.

The compounds according to Example 1 were active in the above test against *Chilo suppressalis*.

EXAMPLE 4

Sterilised compost earth was homogeneously mixed with a wettable powder containing 25% of active substance so that there resulted a rate of application of 8 kg of active substance per hectare.

Young zucchetti plants (*Cucumis pepo*) were put into plastic pots with the treated soil (3 plants per pot; diameter of pot = 7 cm). Each pot was infected immediately aftewards with 5 *Aulacophora femoralis* and Pachmoda or Chortiphila larvae. The control was carried out 4, 8, 16 and 32 days after depositing the larvae.

At 80–100% kill after the first control, a fresh infestation with 5 larvae each was carried out in the same soil sample with 3 new zucchetti plants. If the activity was less than 80%, the remaining larvae remained in the soil sample until the control immediately following. If an active substance at a rate of application of 8 kg/ha still effected a 100% kill, a further control with 4 and 2 kg of active substance per hectare was carried out.

In the above test, the compounds according to Example 1 displayed action against *Aulacophora fermoralis*; Pachmoda and Chortiphila larvae.

EXAMPLE 5

Action against ticks

A. *Rhicephalus bursa*

5 Adult ticks or 50 tick larvae were counted into a glass tube and immersed for 1 to 2 minutes in 2 ml of an aqueous emulsion from an emulsion series each containing 100, 10, 1 and 0.1 ppm of test substance. The tube was then sealed with a standardised cotton wool plug and placed on its head, so that the cotton wool was able to absorb the active substance emulsion.

In the case of the adults evaluation took place after 2 weeks, and in that of the larvae after 2 days. Each test was repeated twice.

The compounds according to Example 1 act in the above test against adults and larvae of *Rhicephalus bursa*.

B. *Boophilus microplus* (larvae)

Tests are carried out in each case with 20 OP-sensitive larvae using an analogous dilution series as in the case of test A. (The resistance relates to the tolerability of diazinone).

The compounds accordng to Example 1 act in the above test against sensitive larvae of *Boophilus microplus*.

EXAMPLE 6

Acaracidal action

*Phaseolus vulgaris* (dwarf beans) have an infested piece of leaf from a mass culture of *Tetranychus urticae* placed on them 12 hours before the test for the acaricidal action. The occupying mobile stages are sprayed with the emulsified test preparations from a chromatography atomiser so that the spray broth does not run off. The number of living and dead larvae, adults and eggs are evaluated after 2 to 7 days under a stereoscopic microscope and the result expressed in percentages. During the "interim", the treated plants are kept in greenhouse compartments at 25°C.

The compounds according to Example 1 are active in the above test against eggs, larvae and adults of *Tetranychus urticae*.

EXAMPLE 7

Action against soil nematodes

To test the action against soil nematodes, the active substance (in a concentration of 50 ppm) is applied to and intimately mixed with soil infected with root gall nematodes (*Meloidgyne avenaria*). Immediately afterwards, tomato cuttings are planted in the thus prepared soil in a series of tests and after a waiting time of 8 days tomato seeds are sown in another test series.

In order to assess the nematocidal action, the galls present on the roots are counted 28 days after planting and sowing respectively. The compounds according to Example 1 display a nematocidal action in the above test.

We claim:

1. An insecticidal or acaricidal composition which contains as the active component an insecticidally or acaricidally effective amount of a compound of the formula

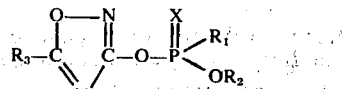

wherein $R_1$ represents $C_1$–$C_4$ alkyl or $C_1$–$C_4$ alkoxy, $R_2$ represents $C_1$–$C_4$ alkyl, $R_3$ represents $C_1$–$C_4$ alkyl, benzyl or phenyl, and X represents sulphur, together with a suitable carrier therefor.

2. A method for combatting insects or acarids which comprises applying to the loci thereof an insecticidally or acaricidally effective amount of a compound of the formula

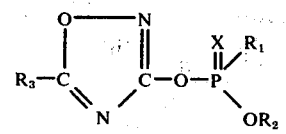

wherein $R_1$ represents $C_1$–$C_4$ alkyl or $C_1$–$C_4$ alkoxy, $R_2$ represents $C_1$–$C_4$ alkyl, $R_3$ represents $C_1$–$C_4$ alkyl, benzyl or phenyl, and X represents sulphur.

3. The method of claim 2, wherein said compound corresponds to the formula

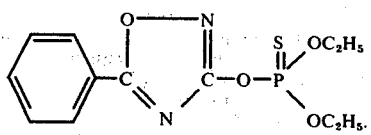

4. The method of claim 2, wherein said compound corresponds to the formula

-continued

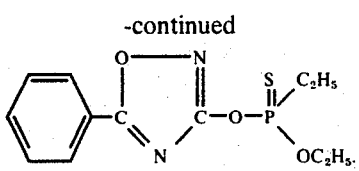

5. The method of claim 2, wherein said compound corresponds to the formula

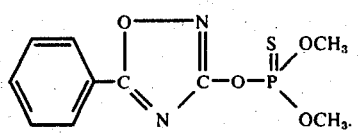

6. The method of claim 2, wherein said compound corresponds to the formula

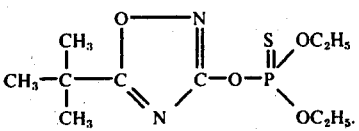

7. The method of claim 2, wherein said compound corresponds to the formula

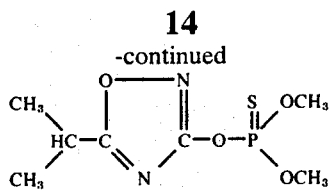

8. The method of claim 2, wherein said compound corresponds to the formula

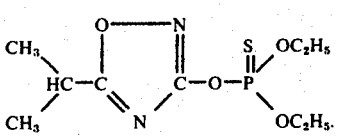

9. The method of claim 2, wherein said compound corresponds to the formula

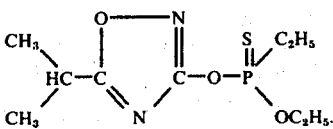

10. The method of claim 2, wherein said compound corresponds to the formula

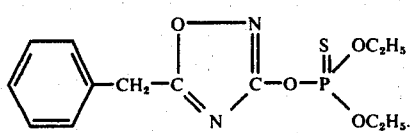

* * * * *